United States Patent [19]
Kajikawa et al.

[11] Patent Number: 5,866,678
[45] Date of Patent: *Feb. 2, 1999

[54] ABSORBENT AND METHOD FOR PRODUCTION OF ABSORBENT RESIN

[75] Inventors: Katsuhiro Kajikawa; Kinya Nagasuna; Yoshihiko Masuda, all of Hyogo, Japan

[73] Assignee: Nippon Shokubai Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 802,284

[22] Filed: Feb. 20, 1997

Related U.S. Application Data

[63] Continuation of Ser. No. 172,388, Dec. 23, 1993, abandoned.

[30] Foreign Application Priority Data

Dec. 25, 1992 [JP] Japan ................................... 4-346578
Dec. 25, 1992 [JP] Japan ................................... 4-346579
Dec. 25, 1992 [JP] Japan ................................... 4-346580

[51] Int. Cl.$^6$ ...................................................... C08F 6/10
[52] U.S. Cl. .......................... 528/487; 528/485; 528/499; 524/430; 524/431; 524/437; 524/450; 521/43; 521/45
[58] Field of Search ................................... 528/487, 485, 528/499; 524/430, 431, 437, 450; 521/43, 45

[56] References Cited

U.S. PATENT DOCUMENTS

| | | | |
|---|---|---|---|
| 4,585,808 | 4/1986 | Reilly | 522/116 |
| 4,766,173 | 8/1988 | Bailey et al. | 524/819 |
| 4,929,717 | 5/1990 | Chmelir | 528/490 |
| 5,229,488 | 7/1993 | Nagasuna et al. | 528/487 |

FOREIGN PATENT DOCUMENTS

| | | |
|---|---|---|
| 0 441 975 A1 | 8/1991 | European Pat. Off. . |
| 0 505 163 A1 | 9/1992 | European Pat. Off. . |
| 37 24 709 C2 | 2/1989 | Germany . |
| 64-24808 | 1/1989 | Japan . |
| 64-62317 | 3/1989 | Japan . |
| WO 91/03497 | 3/1991 | Japan . |

*Primary Examiner*—Marion McCamish
*Assistant Examiner*—John J. Guarriello
*Attorney, Agent, or Firm*—Burns, Doane, Swecker & Mathis, LLP

[57] ABSTRACT

A method for the production of an absorbent resin having a very small residual monomer content either by adding to an absorbent resin powder a substance capable of reacting with the residual monomer in the absorbent resin powder thereby forming an absorbent resin composition having a water content in the range of 10 to 70% by weight and heat-treating the absorbent resin composition at a temperature in the range of 100° to 200 ° C. while retaining the water content of the absorbent resin or by adding to an absorbent resin powder a substance capable of reacting with the residual monomer in the absorbent resin powder thereby forming an absorbent resin composition having a water content in the range of 25 to 55% by weight, heat-treating the absorbent resin composition at a temperature in the range of 120° to 200 ° C. while retaining the water content of the absorbent resin composition in the range mentioned above, and then drying the absorbent resin composition at a temperature not exceeding 120° C.

21 Claims, No Drawings

ABSORBENT AND METHOD FOR PRODUCTION OF ABSORBENT RESIN

This application is a continuation, of application Ser. No. 08/172,388, filed Dec. 23, 1993 abandoned.

BACKGROUND OF THE INVENTION

1. Field of the Invention

This invention relates to an absorbent and a method for the production of an absorbent resin. More particularly, it relates to an absorbent having an extremely low residual monomer content and a method for producing an absorbent resin having a notably low residual monomer content without adversely affecting absorption properties thereto.

2. Description of the Prior Art

In recent years, the use of a various absorbent resins as one component material for sanitary napkin, disposable diaper, and other sanitary products serving to absorb bodily fluids or as an agronomic water-retaining agent has been prevailing.

The absorbent resins of this class heretofore known to the art include partially neutralized cross-linked polyacrylic acid, hydrolyzate of starch-acrylonitrile graft polymer, partially neutralized starch-acrylic acid graft polymer, saponified vinyl acetate-acrylic ester copolymers, and hydrolyzates of acrylonitrile copolymers or acrylamide copolymers or cross-linked materials thereof.

However, these absorbent resins generally suffer persistence of unaltered monomers therein. When these absorbent resins are used in the fields of sanitary products, foodstuffs, etc., it is particularly desirable to lower the residual monomer contents to the fullest possible extent.

Attempts to lower the residual monomers in the polymers have been made for a long time in the field of water-soluble polymers such as, for example, polymeric flocculants. The methods adopted for these attempts are broadly sorted under the following three types as described in JP-A-56-103,207:

(1) A method which relies on increasing the amount of a polymerization initiator or making split addition of the polymerization initiator.

(2) A method which resorts to extraction as with a solvent.

(3) A method which is aimed at changing residual monomers into derivatives other than polymers. These techniques may be applied to the operation of lowering residual monomer contents in the absorbent resins.

Examples of application of the method of (1) to absorbent resins are found in JP-A-56-72,005 AND JP-A-1-24,808. When this method is applied to an absorbent resin, the polymer or absorbent resin shows a decrease in molecular weight of backbone polymer chain, a decrease in absorption capacity due to excessive self-cross-linking reaction, and an increase in a water-soluble content. Thus, the characteristics of the absorbent resin are degraded in spite of a decrease in the residual monomer content.

One example of the method of (2) is found in JP-A-1-292,003. Though this method is indeed effective in lowering the residual monomer content, it can be hardly called a desirable means because it requires use of a large amount of a solvent and entails very costly recovery of the solvent from the polymer.

As typical examples of the method of (3) changing a residual monomer into derivatives other than polymers, a method which resorts to addition of an amine, ammonia, or a similar in the case of a water-soluble polymer (JP-B-33, 2,646) and a method which resorts to addition of a salt of a hydrogen sulfite, a sulfite, a pyrosulfite, or a similar (JP-A-56-103,207), for example, are disclosed. Examples of direct application of this method to absorbent resins are also found in JP-A-1-62,317 and US-A-4,929,717.

Our review of these methods reveals that the polymer obtained by the method disclosed in JP-A-1-62,317 still has a high residual monomer content and the same remark holds good for the method of US-A-4,929,717, that this method is characterized by mixing the polymer with a substance capable of reacting with the residual monomer, adjusting the resultant mixture to a water content in the range of 20 to 90%, and then drying the mixture at a heightened temperature, and that the residual monomer content decreased by this method is still on the level of some tens of ppm, evincing inferiority of the effect of this method. It is preferable to lower the residual monomer eontent of the absorbent resin to the fullest possible extent as described above. The absorbent resins produced by the existing methods suffer persistence of some tens to some hundreds of ppm of residual monomer therein. None of the existing absorbents has attained a decrease of the residual monomer content to below 10 ppm, let alone 5 ppm.

It is, therefore, an object of this invention to provide a novel absorbent and a method for the production of an absorbent resin.

Another object of this invention is to provide an absorbent having a residual monomer at an extremely low concentration and a method for the production of the absorbent resin.

SUMMARY OF THE INVENTION

The objects are accomplished by a method for the treating an absorbent resin comprising (a) a step of adding to an absorbent resin a substance capable of reacting with the residual monomer in the absorbent resin thereby forming an absorbent resin composition having a water content in the range of 10 to 70% by weight and (b) a step of heating the absorbent resin composition at a temperature in the range of 100° to 200° C. for not less than 10 minutes while retaining the ratio of change in water content of the absorbent resin composition within 20%.

The objects are further accomplished by a method for the production of an absorbent resin comprising (a) a step of adding to an absorbent resin powder a substance capable of reacting with the residual monomer in the absorbent resin powder thereby forming an absorbent resin composition having a water content in the range of 25 to 55% by weight, (b) a step of heating the absorbent resin composition at a temperature in the range of 120° to 200° C. for not less than 10 minutes while keeping the water content of the absorbent resin composition in the range mentioned above thereby forming a processed absorbent resin, and (c) a step of drying the processed absorbent resin at a temperature lower than 120° C.

The objects are also accomplished by an absorbent having a residual monomer at a concentration in the range of not more than 5 ppm.

EXPLANATION OF THE PREFERRED EMBODIMENT

The absorbent resin powder to be used in this is invention, when placed in water, absorbs a large amount of water and swells with the absorbed water and forms a hydrogel. As examples of the absorbent resin powder answering this description, those well-known polymers mentioned above may be cited. In consideration of the necessity of decreasing the residual monomer content and the effect of attaining this decrease, it is particularly preferable to use a partially neutralized cross-linked polyacrylic acid in the form of powder.

This invention imposes no particular limit on the form of the absorbent resin. The absorbent resin may be in the form of gel assumed after the step of polymerization and before the step of drying, in the form of powder assumed after the step of both drying and crushing, or in the form of particles having the surface region or vicinity thereof already cross-linked. Among the forms mentioned above, the form of particles having the surface region and vicinity thereof already cross-linked proves particularly preferable. The residual monomer content of the absorbent resin is 10 to 1,000 ppm, preferably 10 to 500 ppm, and more preferably 10 to 300 ppm.

This invention first prepares the absorbent resin composition by virtue of prescribed combination at the step of (a). The substance which is capable of reacting with the residual monomer in the absorbent resin composition must react with the monomer and convert it into a compound other than a polymer thereof. As typical examples of the substance fulfilling the requirement, nitrogen-containing compounds such as ammonia, ammonium salts, hydroxylamines, and amino acids and reducing substances such as sulfurous acid (and salts thereof), hydrogen sulfite (and salts thereof), phosphorous acid (and salts thereof), pyrosulfurous acids (and salts thereof), hypophosphorous acid (and salts thereof), and thiosulfuric acid (and salts thereof) may be cited. In the light of the ability to lower the residual monomer content, such reducing substances as sulfurous acid (and salts thereof), hydrogen sulfite (and salts thereof), pyrosulfurous acid (and salts thereof), and thiosulfuric acid (and salts thereof) prove particularly preferable.

In the first aspect of this invention, the absorbent resin at the step of (a) must possess a water content in the range of 10 to 70% by weight. The adjustment of the absorbent resin with respect to the water content may be made at any desired time. For example, this adjustment may be carried out before, after, or during the addition of the substance capable of reacting with the residual monomer to the absorbent resin. The preparation of the absorbent resin is carried out more often than not by solution polymerization or reversed-phase suspension polymerization of the water-soluble monomer. These methods of polymerization are invariably carried out generally in the presence of water. When the absorbent resin which is obtained by such a method of polymerization as mentioned above has a water content in the range of 10 to 70% by weight, it may be used in its unmodified form at the step of (a). In this case, when the substance capable of reacting with the residual monomer in the absorbent resin is added just before the process of polymerization is completed, it is permissible to consider the step of (a) to be done in the process of polymerization. The absorption resin composition which is obtained as described above may be continuously subjected to the step of (b). Of course, it is permissible to polymerize the water-soluble monomer under conditions deviating from the ranges specified herein and then add water to the resultant polymer or dry the polymer so as to adjust the conditions to the ranges. When the absorbent resin is a dry powder, water must be added to the absorbent resin to adjust the water content thereof to a level in the range of 10 to 70% by weight. This addition of water may be effected by using in place of water an aqueous solution obtained by dissolving the substance capable of reacting with the residual monomer in water, by adding the substance capable of reacting with the residual monomer prior to the addition of water, or by adding the substance capable of reacting with the residual monomer subsequently to the addition of water.

The ratio of decrease of the residual monomer is unduly low if the water content is less than 10% by weight. This ratio is similarly low if the water content exceeds 70% by weight. The unduly large amount of water renders the method of processing under discussion uneconomical because the amount of energy to be required for drying is unduly large. Preferably, the water content is in the range of 20 to 50% by weight.

It is very important that the absorbent resin composition of a water content in the range of 10 to 70% by weight, preferably 20 to 60% by weight, more preferably 30 to 50% by weight obtained at the step of (a) should be heated while keeping the ratio of change of the water content below the prescribed level. In this case, the residual monomer is notably decreased by keeping the ratio of change in the water content below 20%, preferably below 10%, more preferably below 1%.

By the conventional method, the absorbent resin to which the substance capable of reacting with the residual monomer has been added is immediately subjected to a drying treatment. This invention contemplates exposing the absorbent resin in the same state avoiding water evaporation to a high temperature for a stated duration.

As a result of the treatment described above, the residual monomer content is notably decreased. As respects the conditions for the treatment under discussion, it has been ascertained that the notable decrease of the residual monomer is obtained by causing the absorbent resin to stand at an elevated temperature in the range of 100° C. to 200° C., preferably 120° C. to 180° C., and more preferably 140° C. to 160° C. for a period in the range of 10 minutes to 10 hours, preferably 30 minutes to 5 hours, and more preferably 1 to 3 hours, while retaining the ratio of change of the water content below 20%, desirably below 10%, and more desirably below 1%.

So long as the conditions fall within the respective ranges specified above, no particular restriction is imposed on the kind of heating means to be used at the step of (b). As typical examples of the heating method, a method which effects the heating in a tightly closed atmosphere, a method which effects conductive heating in an open system, and a method which effects the heating by spraying steam may be cited. The devices which can be effectively used for the heating in a tightly closed atmosphere include autoclaves, (pressure) channel type stirring heaters, (pressure) rotary heaters, (pressure) disc heaters, (pressure) fluidized-bed heaters, (pressure) air current heaters, (pressure) infrared heaters, (pressure) hot air heaters, and (pressure) microwave heaters, for example.

The second aspect of this invention requires the absorbent resin to acquire a water content in the range of 25 to 55% by weight at the step of (a). The adjustment to this water content may be carried out at any desired time. For example, it may be made before, after, or during the addition to the absorbent resin of the substance capable of reacting with the residual monomer in the absorbent resin. The absorbent resin is produced more often than not by solution polymerization or reversed-phase suspension polymerization of a water-soluble monomer. These polymerizations are generally carried out in the presence of water. When the absorbent resin obtained by such a method of polymerization has a water content in the range of 25 to 55% by weight, it may be used in its unmodified form at the step of (a). In this case, when the substance capable of reacting with the residual monomer in the absorbent resin is added just before the process of polymerization is completed, it is permissible to regard the step of (a) to be done in the process of polymerization. The absorbent resin composition which is obtained as described above may be subjected continuously to the step of (b). It is naturally permissible to polymerize the water-soluble monomer under conditions deviating from the range specified herein and then either add water to the resultant polymer or dry the polymer so as to adjust the conditions to the range. When the absorbent resin is a dry powder, water must be added in order to adjust the water content thereof in the range of 25 to 55% by weight. In this case, the addition of water just mentioned may be effected by using in place of water an aqueous solution having the substance capable of reacting with the residual monomer dissolved in water, by adding the substance capable of reacting with the residual monomer prior to the addition of water, or by first adding water and then adding the substance capable of reacting with the residual monomer.

The ratio of decrease of the residual monomer is unduly low if the water content is less than 25% by weight. This ratio is similarly low if the water content exceeds 55% by weight. The unduly large amount of water renders the method of processing under discussion uneconomical because the amount of energy to be required for drying is unduly large. Preferably, the water content is in the range of 35 to 45% by weight.

The absorbent resin composition of a water content in the range of 25 to 55% by weight, preferably 35 to 45 by weight, which has been obtained by the treatment of the step of (a) is heated at a temperature In the range of 120° to 200° C. for not less than 10 minutes while keeping the water content thereof in the range mentioned above at the step of (b). For this invention, it is very important that the water content should be kept in the range of 25 to 55% by weight while the heating is in progress. The fulfillment of this requirement brings about a conspicuous decrease of the residual monomer. Ideally, this heat treatment is carried out at a temperature in the range of 120° to 200° C., preferably 150° to 170° C., for a period of not less than 10 minutes, preferably not less than 30 minutes, and more preferably not less than one hour. Though no upper limit is particularly set for the heating time, the duration of this heat treatment is generally not more than 10 hours. If the heat treatment is carried out for more than 10 hours, the excess of heating time brings about no proportionate addition to the effect but rather entails the possibility of degrading the quality of the absorbent resin. This heating time is preferably not more than five hours, more preferably not more than three hours. The processed absorbent resin is then dried at a temperature of less than 120° C. at the next step of (c). By the conventional method, the drying is generally carried out at a high temperature. When the drying is conducted at a high temperature, the disadvantage arises that the residual monomer content already lowered at the preceding step is increased again. For this invention, therefore, the drying must be carried out at a temperature of less than 120° C. For the purpose of further enhancing the effect of the heat treatment, it is preferable to set this temperature in the range of 50° to 100° C., preferably 60° to 80° C.

When the conditions mentioned above fall in the ranges specified by the invention, no particular limit is imposed on the heating means to be adopted at the step of (b). As typical examples of the heating method, a method which effects the heating in a tightly closed atmosphere, a method which effects conductive heating in an open system, and a method which effects the heating by spraying steam may be cited. The devices which can be effectively used for the heating in a tightly closed atmosphere are the same as those cited previously as usable in the first aspect of this invention.

For the drying at the step of (c), any of the well-known devices heretofore available for the kind of drying under discussion may be adopted. When the heating device used at the step of (b) is used also as drying means under due operating conditions, the heating device used at the step of (b) may be identical with the drying device used at the step of (c). The step of (a) and the step of (b) both may be carried out either continuously or batchwise.

For this invention, it is very important that the step of (b) for heating the absorbent resin composition should be carried out at as high a temperature as possible and the step of (c) for drying the processed absorbent resin should be carried out at as low a temperature as permissible.

In the first and second aspects of this inventions the absorbent resin composition is allowed to incorporate therein suitable additives for the purpose of accomplishing the object and effect of this invention at a still higher level.

As typical examples of the additives, inorganic and/or organic water-insoluble particulate substances, surfactants, and dispersants like organic solvents may be cited.

The water-insoluble particulate substances include inorganic water-insoluble minute particles such as of silicon dioxide, titanium dioxide, aluminum oxide, magnesium oxide, zinc oxide, talc, calcium phosphate, barium phosphate, clay, diatomaceous earth, zeolite, bentonite, kaolin, hydrotalcite, and activated clay and organic water-insoluble minute particles such as of cellulose, ground pulp, ethyl cellulose, ethyl hydroxyethyl cellulose, cellulose acetate, modified starch, chitin, rayon, polyester, polyethylene, polypropylene, polyvinyl chloride, polystyrene, nylon, polymethyl methacrylate, melamine resin, melamine-benzoguanamine resin, activated carbon, and tea leaves, for example. These water-insoluble particulate substances can be used either singly or in the form of a mixture of two or more members.

These water-insoluble particulate substances are required to have a particle diameter in the range of 0.01 to 1,000 $\mu$m, preferably 0.01 to 50 $\mu$m, and more preferably 0.01 to 10 $\mu$m. In all of these water-insoluble particulate substances, inorganic water-insoluble particulate substances prove desirable. Among other inorganic water-insoluble particulate substances, silicon dioxide, titanium dioxide, aluminum oxide, zeolite, kaolin, and hydrotalcite prove particularly desirable. Such inorganic particulate substances as sepiolite which possess a deodorizing function can be used particularly advantageously in this invention. Among other organic water-insoluble particulate substances cited above, pulp, ground cellulose, methyl methacrylate particles having a particle diameter of not more than 5 $\mu$m such as, for example, powdered polymethyl methacrylate, and activated carbon prove particularly preferable. When these water-insoluble particulate substances have undergone a treatment for partial deprivation of hydrophilicity, they can be used advantageously in this invention.

The surfactants which are effectively usable herein include anionic surfactants, nonionic surfactants, cationic surfactants, amphoteric surfactants, and polymeric surfactants, for example. These surfactants can be used either singly or in the form of a mixture of two or more members.

The anionic surfactants include higher alcohol sulfuric esters, alkyl naphthalene sulfonates, alkyl polyoxyethylene sulfates, and dialkyl sulfosuccinates, for example; the nonionic surfactants include sorbitan fatty acid esters, polyoxyethylene sorbitan fatty acid esters, (poly)glycerol fatty acid esters, polyoxy-ethylene alkyl ethers, polyoxyethylene alkylphenol ethers, polyoxyethylene acyl esters, and sucrose fatty acid esters, for example; the cationic surfactants include alkyl quaternary ammonium salts and alkylamine salts, for example; the amphoteric surfactants include alkyl betaines and lecithins, for example; and the macromolecular surfactants include oleophilic carboxyl group-containing polymers and ethylene oxide-propylene oxide block polymers, for example.

In these surfactants, those of the water-soluble and/or water-dispersible type prove preferable in excelling in the effect of decreasing the residual monomer content without impairing the final product's ability to absorb liquid. Among other water-soluble and/or water-dispersible surfactants, anionic surfactants or nonionic surfactants having an HLB value of not less than 7, preferably an HLB value of not less than 10, are particularly advantageously usable.

The organic solvents which are effectively used herein include hydrophilic organic solvents such as methanol, ethanol, isopropanol, butanol, ethylene glycol monomethyl ether, ethylene glycol monoethyl ether, propylene glycol monomethyl ether, tetrahydrofuran, dimethyl formamide, dimethyl sulfoxide, acetone, and methylethyl ketone and hydrophobic organic solvents such as n-pentane, n-heptane, n-octane, cyclohexane, cyclooctane, methyl cyclohexane, Decalin, benzene, ethyl benzene, toluene, and xylene, for example. The hydrophilic organic solvents are preferred over the hydrophobic organic solvents.

When the absorbent resin powder to be used in working this invention is such in form that the powder obtained by drying and pulverizing the absorbent resin or the surface region or vicinity thereof is in a cross-linked state, the residual monomer content can be decreased to a greater extent when the water-insoluble particulate substance, the surfactant, and the organic solvent mentioned above are used than when they are not used. Generally, the amount of the water-insoluble particulate substance to be used is in the range of 0.01 to 5 parts by weight, preferably 0.5 to 2 parts by weight, that of the surfactant in the range of 0.01 to 5 parts by weight, preferably 0.5 to 2 parts by weight, and that of the organic solvent in the range of 0.01 to 8 parts by weight, preferably 0.1 to 5 parts by weight, respectively based on 100 parts by weight of the absorbent resin to be treated.

Further, the absorbent resin which is obtained by this invention may be endowed with new functions by having such additives as deodorant, perfume, chemical agent, plant growth promoter, fungicide, foaming agent, pigment, dye, hydrophilic filaments, or fertilizer incorporated therein.

The absorbent obtained by the method described above has a residual monomer content of not more than 5 ppm, preferably in the range of 0.01 to about 2 ppm.

Now, the present invention will be further described below with reference to working examples. It should be noted that the scope of this invention is not limited to these working examples. Wherever the word "parts" is mentioned in the working examples, it refers to "parts by weight" unless otherwise specified.

The residual monomer content, the water content, and the ratio of change in water content which are described in the working examples were determined as follows.
(1) Residual monomer content In a beaker having an inner volume of 200 ml, 100 ml of deionized water was wholly gelled by stirring the deionized water and 1.0 g of a given absorbent resin added thereto together. One hour thereafter, the gel was shrunk by the addition of 5 ml of an aqueous phosphoric acid solution and stirred. The absorbent resin dispersion consequently formed was passed through a filter paper. The filtrate was analyzed by the technique of high performance liquid chromatography.

Separately, a calibration curve was prepared by similarly analyzing standard monomer solutions of known concentrations. The amount of residual monomer in the absorbent resin was found by using the calibration curve as an external standard and taking into due consideration the ratio of dilution of the filtrate. (The residual monomer contents to be indicated hereinafter are invariably numerical values to solid content, taking water content into consideration.)
(2) Water content The water content of a given absorbent resin composition was determined by allowing a sample of the composition to stand in a drying device at 180° C. for three hours, weighing the dried sample, and finding the decrease in weight and reporting this decrease.
(3) Ratio of change in water content This magnitude was found by allowing a sample of a given absorbent resin composition to stand in a drying device at 180° C. for three hours thereby determining the water content of the absorbent resin composition and performing calculation of the following formula using the water contents before and after the heat treatment.

Ratio of change in water content(%) ={[(Water content after heat treatment)−(Water content before heat treatment)]/(Water content before heat treatment)}× 100

REFERENTIAL EXAMPLE

A solution was prepared by dissolving 141 parts of sodium acrylate, 36.1 parts of acrylic acid, and 0.093 part of N,N'-methylene bis-acrylamide in 329 parts of deionized water and deprived of dissolved oxygen by blowing nitrogen gas therein. The resultant aqueous monomer solution was kept at 30° C. Then, the aqueous monomer solution and 0.6 part of sodium persulfate and 0.01 part of l-ascorbic acid added thereto were subjected together to stationary polymerization to obtain a gel hydrated polymer.

This polymer was dried with hot air at 150° C., pulverized with a hammer type crusher, and sifted with a 20-mesh metallic screen to obtain a thru-20 mesh absorbent resin powder (A). This absorbent resin was found to have a residual monomer content of 223 ppm.

Then, by mixing 100 parts by weight of the absorbent resin powder (A) with an aqueous liquid consisting of 1 part by weight of glycerin, 4 parts by weight of water, and 4 parts by weight of ethanol and heat-treating the resultant mixture at 180° C. for 30 minutes, an absorbent resin powder (B) having the surface region and vicinity thereof cross-linked was obtained. This absorbent resin powder (B) was found to have a residual monomer content of 230 ppm.

EXAMPLE 1

One hundred (100) parts of the absorbent resin powder (B) prepared in Referential Example was mixed with 1.0 part of silicon dioxide (produced by Japan Aerosil K. K. and marketed under trademark designation of "Aerosil 100"). An aqueous liquid of reducing substance was prepared by dissolving 1 part of sodium hydrogen sulfite as a reducing substance in 60 parts of water and 8 parts of isopropanol. This aqueous liquid was mixed with the mixture of the absorbent resin powder (B) with silicon dioxide by the use of a high-speed paddle type mixing device. The absorbent resin composition consequently obtained was found to have a water content of 37.5% by weight.

Then, the absorbent resin composition was placed in a cylindrical vessel (1) measuring 10 cm in inside diameter and 10 cm in length, tightly sealed therein, and heat-treated in a furnace at 150° C. for one hour. After the heat treatment, the absorbent resin composition was found to have a water content of 37.1% by weight, a ratio of change of-1% in water content, and a residual monomer content of 0.4 ppm. Subsequently, the absorbent resin composition was removed from the vessel, heat-treated at 100° C. for 3 hours, and sifted with a 20-mesh metallic screen to obtain a thru-20 mesh absorbent. This absorbent was found to have a residual monomer content of 1.4 ppm.

EXAMPLE 2

One hundred (100) parts of the absorbent resin (B) obtained in Referential Example was mixed with 0.7 part of sodium dialkyl sulfosuccinate (produced by Kao Soap Co., Ltd. and marketed under trademark designation of "Pelex OT-P") as a surfactant. By the use of a high-speed paddle type mixing device, a solution of 1 parts of sodium hydrogen sulfite as a reducing substance in 200 parts of water was mixed with the mixture of the absorbent resin (B) with the surfactant. The absorbent resin composition consequently obtained was found to have a water content of 66.7% by weight.

Then, this absorbent resin composition was placed in a cylindrical vessel (1) measuring 10 cm in inside diameter and 10 cm in length, tightly sealed therein, and heat-treated in a furnace at 200° C. for 10 hours. After the heat treatment, the absorbent resin composition was found to have a water content of 55.3% by weight, a ratio of change of-17% in water content, and a residual monomer content of 1.2 ppm. Subsequently, the absorbent resin composition was removed from the vessel, heat-treated in a fluidized-bed drying device at 80° C. for 3 hours, and sifted with a 20-mesh metallic screen to obtain a thru-20 mesh absorbent. This absorbent was found to have a residual monomer content of 1.3 ppm.

EXAMPLE 3

One hundred (100) parts of the absorbent resin obtained in Referential Example was mixed with 1.0 part of silicon dioxide treated to be endowed with hydrophobicity (produced by Japan Aerosil K. K. and marketed under trademark designation of "Aerosil R972"). An aqueous liquid of reducing substance was prepared by dissolving 2 parts of sodium thiosulfate as a reducing substance in 20 parts of water. By the use of a high-speed paddle type mixing device, this aqueous liquid was mixed with the mixture of the absorbent resin (B) with the hydrophobic silicon dioxide. The absorbent resin composition consequently obtained was found to have a water content of 16.5% by weight.

Then, this absorbent resin composition was placed in a cylindrical vessel (1) measuring 10 cm in inside diameter and 10 cm in, length, tightly sealed therein, and heat-treated in a furnace at 180° C. for five hours. After the heat treatment, the absorbent resin composition was found to have a water content of 15.7% by weight, a ratio of change of-5% in water content, and a residual monomer content of 1.0 ppm. Subsequently, the absorbent resin composition was removed from the vessel, dried with hot air at 100° C. for 3 hours, and sifted with a 20-mesh metallic screen to obtain a thru-20 mesh absorbent. This absorbent was found to have a residual monomer content of 1.9 ppm.

EXAMPLE 4

One hundred (100) parts of the absorbent resin (B) obtained in Referential Example was mixed with 2.0 parts of aluminum oxide (produced by Degussa K. K. and marketed under trademark designation of "Aluminum Oxide C"). An aqueous liquid of reducing substance was prepared by dissolving 1 part of sodium sulfite as a reducing substance in 40 parts of water and 2 parts of ethanol. By the use of a high-speed paddle type mixing device, the aqueous liquid was mixed with the mixture of the absorbent resin (B) with aluminum oxide. The absorbent resin composition consequently obtained was found to have a water content of 28.6% by weight.

Then, this absorbent resin composition was placed in a cylindrical vessel (1) measuring 10 cm in inside diameter and 10 cm in length, tightly sealed therein, and heat-treated in a furnace at 120° C. for 10 hours. After the heat treatment, the absorbent resin composition was found to have a water content of 28.6% by weight, a ratio of change of 0% in water content, and a residual monomer content of 0.9 ppm. Subsequently, the absorbent resin composition was removed from the vessel, heat-treated in a fluidized-bed drying device at 80° C. for 3 hours, and sifted with a 20-mesh metallic screen to obtain a thru-20 mesh absorbent. This absorbent was found to have a residual monomer content of 1.0 ppm.

EXAMPLE 5

One hundred (100) parts of the absorbent resin (B) obtained in Referential Example was mixed with 2.0 parts of activated carbon. An aqueous liquid of reducing substance was prepared by dissolving 1 part of monoethanol amine as a reducing substance in 70 parts of water and 2 parts of isopropanol. By the use of a high-speed paddle type mixing device, this aqueous liquid was mixed with the absorbent resin (B) with the activated carbon. The absorbent resin composition consequently obtained was found to have a water content of 41.2% by weight.

Then, this absorbent resin composition was placed in a furnace adapted to admit a blown stream of steam and heat-treated therein with the introduced steam at 140° C. for 30 minutes. After the heat treatment, the absorbent resin composition was found to have a water content of 46.0% by weight, a ratio of change of 12% in water content, and a residual monomer content of 0.9 ppm. Subsequently, the absorbent resin composition was removed from the furnace, dried with hot air at 100° C. for 3 hours, and sifted with a 20-mesh metallic screen to obtain a thru-20 mesh absorbent. This absorbent was found to have a residual monomer content of 1.5 ppm.

EXAMPLE 6

One hundred (100) parts of the absorbent resin obtained in Referential Example was mixed with 2.0 parts of fine powder of polymethyl methacrylate. By the use of a high-speed paddle type mixing device, a solution of 1 part of sodium hydrogen sulfite as a reducing substance in 60 parts of water was mixed with the mixture of the absorbent resin (B) with polymethyl methacrylate. The absorbent resin composition consequently formed was found to have a water content of 37.5% by weight.

Then, this absorbent resin composition was placed in a cylindrical vessel (1) measuring 10 cm in inside diameter and 10 cm in length, tightly sealed therein, and heat-treated in a furnace at 100° C. for 10 minutes. After the heat treatment, the absorbent resin composition was found to have a water content of 37.5% by weight, a ratio of change of 0% in water content, and a residual monomer content of 1.9 ppm. Subsequently, the absorbent resin composition was removed from the furnace, heat-treated in a fluidized-bed drying device at 80° C. for 3 hours, and sifted with a 20-mesh metallic screen to obtain a thru-20 mesh absorbent. This absorbent was found to have a residual monomer content of 1.9 ppm.

EXAMPLE 7

In 329 parts of deionized water, 141 parts of sodium acrylate, 36.1 parts of acrylic acid, and 0.093 part of N,N'-methylene bis-acrylamide were dissolved. The resultant solution was deprived of dissolved oxygen by introducing a blown stream of nitrogen gas. The aqueous monomer solution was kept at 30° C. Then, the aqueous solution and 0.6 part of sodium persulfate and 0.01 part of l-ascorbic acid added thereto were subjected together to stationary polymerization to obtain a gel hydrated polymer. This gel polymer was found to have a residual monomer content of 1.2%. In a twin-arm kneader, 100 parts by weight of this gel polymer as solids and 3 parts of sodium sulfite added thereto were mixed.

Then, the gel polymer having a water content of 65.0% by weight was removed from the kneader, placed in a cylindrical vessel (1) measuring 10 cm in inside diameter and 10 cm in length, tightly sealed therein, and heat-treated in a furnace at 150° C. for two hours. After the heat treatment, the gel polymer was found to have a water content of 62.0% by weight, a ratio of change of-5% in water content, and a residual monomer content of 1.3 pp Subsequently, the absorbent resin composition was removed from the vessel, dried with hot air at 120° C. for two hours, pulverized with a crushing device, and sifted with a 20-mesh metallic screen to obtain a thru-20 mesh absorbent. The absorbent was found to have a residual monomer content of 1.9 ppm.

EXAMPLE 8

One hundred (100) parts of the absorbent resin powder (B) prepared in Referential Example was mixed with 1.0 part of silicon dioxide treated to be endowed with hydrophobicity (produced by Japan Aerosil K. K. and marketed under trademark designation of "Aerosil B972"). Two parts of sodium sulfite was dissolved in 70 parts of water to prepare an aqueous solution of a reducing substance. The aqueous solution was added and mixed with the hydrophobically treated silicon dioxide using the high-speed paddle type mixing device. Water content of the absorbent resin composition thus obtained was 41.5% by weight.

Then the absorbent resin composition was charged to a well closed paddle drier which was heated at a temperature of 120° C., and a part of the absorbent resin composition was removed after 10 minutes. Water content of the absorbent resin composition thus treated was 34.2% by weight (a ratio of change in water content was –17.6%) and residual monomer content was 0.81 ppm. Then the absorbent resin composition was continuously heated without closure for 2 hours to dry. Water content of the absorbent after heat treatment was 8.5% by weight and residual monomer content was 0.92 ppm.

EXAMPLE 9

One hundred (100) parts of the absorbent resin powder (B) prepared in Referential Example was mixed with 1.0 part of silicon dioxide (produced by Japan Aerosil K. K. and marketed under trademark designation of "Aerosil 100"). An aqueous liquid of reducing substance was prepared by dissolving 1 part of sodium hydrogen sulfite as a reducing substance in 60 parts of water and 8 parts of isopropanol. This aqueous liquid was mixed with the mixture of the absorbent resin powder (B) with silicon dioxide by the use of a high-speed paddle type mixing device. The absorbent resin composition consequently obtained was found to have a water content of 37.5% by weight.

Then, the absorbent resin composition was placed in a cylindrical vessel (2) measuring 10 cm in inside diameter and 10 cm in length, tightly sealed therein, and heat-treated in a furnace at 150° C. for 1 hour. After the heat treatment, the absorbent resin composition (processed absorbent resin) was found to have a water content of 28.9% by weight and a residual monomer content of 0.89 ppm. Subsequently, the absorbent resin composition was removed from the vessel, dried with hot air at 80° C. for 3 hours, and sifted with a 20-mesh metallic screen to obtain a thru-20 mesh absorbent resin. This absorbent resin was found to have a residual monomer content of 0.92 ppm.

EXAMPLE 10

One hundred (100) parts of the absorbent resin powder (B) obtained in Referential Example was mixed with 0.7 part of sodium dialkyl sulfosuocinate as a surfactant (produced by Kao Soap Co., Ltd. and marketed under trademark designation of "Pelex OT-P"). A solution prepared by dissolving 1 part of sodium hydrogen sulfite as a reducing substance in 33 parts of water was mixed with the mixture of the absorbent resin powder (B) with the surfactant by the use of a high-speed paddle type mixing device. The absorbent resin composition consequently formed was found to have a water content of 25.0% by weight.

Then, the absorbent resin composition was placed in a cylindrical vessel (2) measuring 10 cm in inside diameter and 10 cm in length, tightly sealed therein, and heat-treated in a furnace at 140° C. for 10 hours. After the heat treatment, the absorbent resin composition (processed absorbent resin) was found to have a water content of 24.8% by weight and a residual monomer content of 0.83 ppm. Subsequently, the absorbent resin composition was removed from the vessel, heat-treated with a fluidized-bed drying device at 60° C. for 5 hours, and sifted with a 20-mesh metallic screen to obtain a thru-20 mesh absorbent resin. This absorbent resin was found to have a residual monomer content of 0.84 ppm.

EXAMPLE 11

One hundred (100) parts of the absorbent resin powder (B) obtained in Referential Example was mixed with 1.0 part of silicon dioxide treated to be endowed with hydrophobicity (produced by Japan Aerosil K. K. and marketed under trademark designation of "Aerosil R972"). An aqueous liquid of a reducing substance was prepared by dissolving 2 parts of sodium thiosulfate as a reducing substance in 67 parts of water. This aqueous liquid was mixed with the mixture of the absorbent resin powder (B) with the hydrophobic silicon dioxide by the use of a high-speed paddle type mixing device. The absorbent resin composition consequently obtained was found to have a water content of 40.2% by weight.

Then, this absorbent resin composition was placed in a cylindrical vessel (2) measuring 10 cm in inside diameter and 10 cm in length, tightly sealed therein, and heat-treated in a furnace at 160° C. for 30 minutes. After the heat treatment, the absorbent resin composition (processed absorbent resin) was found to have a water content of 34.2% by weight and a residual monomer content of 0.56 ppm. Subsequently, the absorbent resin composition was removed from the vessel, dried with hot air at 70° C. for 5 hours, and sifted with a 20-mesh metallic screen to obtain a thru-20 mesh absorbent. This absorbent was found to have a residual monomer content of 0.56 ppm.

EXAMPLE 12

One hundred (100) parts of the absorbent resin powder (B) obtained in Referential Example was mixed with 2.0 parts of aluminum oxide (produced by Degussa K. K. and marketed under trademark designation of "Aluminum Oxide C"). An aqueous liquid of a reducing substance was prepared by dissolving 1 part of sodium sulfite as a reducing substance in 120 parts of water and 2 parts of ethanol. This aqueous liquid was mixed with the mixture of the absorbent resin powder (B) with the aluminum oxide by the use of a high-speed paddle type mixing device. The absorbent resin composition consequently obtained was found to have a water content of 54.7% by weight.

Then, the absorbent resin composition was placed in a cylindrical vessel (2) measuring 10 cm in inside diameter and 10 cm in length, tightly sealed therein, and heat-treated in a furnace at 180° C. for 10 hours. After the heat treatment, the absorbent resin composition (processed absorbent resin) was found to have a water content of 35.2% by weight and a residual monomer content of 0.71 ppm. Subsequently, the absorbent resin composition was removed from the vessel, heat-treated in a fluidized-bed drying device at 80° C. for 3 hours, and sifted with a 20-mesh metallic screen to obtain a thru-20 mesh absorbent resin. This absorbent resin was found to have a residual monomer content of 0.75 ppm.

EXAMPLE 13

One hundred (100) parts of the absorbent resin powder (B) obtained in Referential Example was mixed with 2.0 parts of activated carbon. An aqueous liquid of a reducing substance was prepared by dissolving 1 part of sodium sulfite as a reducing substance in 54 parts of water and 2 parts of isopropanol. This aqueous liquid was mixed with the mixture of the absorbent resin powder (B) with the activated carbon by the use of a high-speed paddle type mixing device. The absorbent resin composition consequently obtained was found to have a water content of 35.0% by weight.

Then, this absorbent resin was placed in a furnace of the type adapted to admit a blown stream of steam and heat-treated therein with the introduced steam at 120° C. After the heat treatment, the absorbent resin composition (processed absorbent resin) was found to have a water content of 40.2% by weight and a residual monomer content of 0.53 ppm. Thereafter, the absorbent resin composition was removed from the vessel, dried with hot air at 50° C. for 10 hours, and sifted with a 20-mesh metallic screen to obtain a thru-20 mesh absorbent resin. This absorbent resin was found to have a residual monomer content of 0.53 ppm.

EXAMPLE 14

One hundred (100) parts of the absorbent resin powder (B) obtained in Referential Example was mixed with 2.0 parts of a fine powder of polymethyl methacrylate. A solution was prepared by dissolving 1 part of sodium hydrogen sulfite as a reducing substance in 60 parts of water. The resultant solution was mixed with the mixture of the absorbent resin powder (B) with polymethyl methacrylate by the use of a high-speed paddle type mixing device. The absorbent resin composition consequently obtained was found to have a water content of 37.5% by weight.

Then, this absorbent resin composition was placed in a cylindrical vessel (2) measuring 10 cm in inside diameter and 10 cm in length, tightly sealed therein, and heat-treated in a furnace at 200° C. for 10 minutes. After the heat treatment, the absorbent resin composition (processed absorbent resin) was found to have a water content of 35.2% by weight and a residual monomer content of 0.27 ppm. Subsequently, the absorbent resin composition was removed from the vessel, heat-treated in a fluidized-bed drying device at 120° C. for 2 hours, and sifted with a 20-mesh metallic screen to obtain a thru-20 mesh absorbent resin. This absorbent resin was found to have a residual monomer content of 0.93 ppm.

Control 1

One hundred (100) parts of the absorbent resin powder (B) obtained in Referential Example was mixed with an aqueous liquid having 0.3 part of sodium hydrogen sulfite dissolved in 5 parts of water by the use of a high-speed paddle type mixing device. The absorbent resin for comparison consequently obtained was found to have a residual monomer content of 21.0 ppm.

Control 2

One hundred (100) parts of the absorbent resin powder (B) obtained in Referential Example was mixed with a solution of 1 part of hydroxyl amine hydrochloride in 50 parts of water by the use of a high-speed paddle type mixing device. The absorbent resin composition consequently obtained was found to have a water content of 33.3% by weight. This absorbent resin composition was removed from the mixing device, dried with hot air at 120° C. for 2 hours, and sifted with a 20-mesh metallic screen to obtain a thru-20 mesh absorbent. This absorbent resin for comparison was found to have a water content of 2.7% by weight, a ratio of change of -92% in water content, and a residual monomer content of 80.3 ppm.

Control 3

One hundred (100) parts of the absorbent resin powder (B) obtained in Referential Example and a solution of 5 parts of sodium hydrogen sulfite in 300 parts of water were mixed by the use of a high-speed paddle type mixing device. The absorbent resin composition consequently obtained was found to have a water content of 75.2% by weight. This absorbent resin composition was removed from the mixing device, dried with hot air at 120° C. for two hours, and sifted with a 20-mesh metallic screen to obtain a thru-20 mesh absorbent. This absorbent resin for comparison was found to have a water content of 3.3% by weight, a ratio of change of -96% in water content, and a residual monomer content of 33.4 ppm.

Control 4

One hundred (100) parts of the absorbent resin powder (B) obtained in Referential Example was mixed with 1.0 part of silicon dioxide treated to be endowed with hydrophobicity (produced by Japan Aerosil K. K. and marketed under trademark designation of "Aerosil R972"). An aqueous liquid of a reducing substance was prepared by dissolving 2 parts of sodium thiosulfate as a reducing substance in 20 parts of water. This aqueous liquid was mixed with the mixture of the absorbent resin powder (B) with the hydrophobic silicon dioxide by the use of a high-speed paddle type mixing device. The absorbent resin composition consequently obtained was found to have a water content of 16.7% by weight. Then, this absorbent resin composition was removed from the mixing device, dried with hot air at 110° C. for 10 hours, and sifted with a 20-mesh metallic screen to obtain a thru-20 mesh absorbent resin for comparison. This absorbent resin for comparison was found to have a water content of 8.6% by weight, a ratio of change of −49% in water content, and a residual monomer content of 62.5 ppm.

Control 5

An aqueous liquid of reducing substance was prepared by dissolving 1 part of sodium thiosulfate as a reducing substance in 1,900 parts of water. This aqueous liquid was mixed with 100 parts of the absorbent resin powder (B) obtained in Referential Example by the use of a twin-arm kneader. The absorbent resin composition consequently obtained was found to have a water content of 95.0% by weight.

Then, this absorbent resin composition was placed in a cylindrical vessel (1) measuring 10 cm in inside diameter and 10 cm in length, tightly sealed therein, and heat-treated in a furnace at 150° C. for one hour. After the heat-treatment, the absorbent resin composition (processed absorbent resin) was found to have a water content of 76.2% by weight, a ratio of change of −20% in water content, and a residual monomer content of 14.2 ppm. Subsequently, the processed absorbent resin was removed from the vessel, dried with hot air at 150° C. for three hours, and sifted with a 20-mesh metallic screen to obtain a thru-20 mesh absorbent resin for comparison. The absorbent resin for comparison was found to have a residual monomer content of 31.6 ppm.

Control 6

One hundred (100) parts of the absorbent resin powder (B) obtained in Referential Example was mixed with 2.0 parts of aluminum oxide (produced by Degussa K. K. and marketed under trademark designation of "Aluminum Oxide C"). An aqueous liquid of reducing substance was prepared by dissolving 1 part of sodium sulfite as a reducing substance in 40 parts of water and 2 parts of ethanol. By the use of a high-speed paddle type mixing device, this aqueous liquid was mixed with the mixture of the absorbent resin powder (B) with aluminum oxide. The absorbent resin composition consequently obtained was found to have a water content of 28.6% by weight.

Then, this absorbent resin composition was placed in a cylindrical vessel (1) measuring 10 cm in inside diameter and 10 cm in length, tightly sealed therein, and heat-treated in a furnace at 80° C. for 30 minutes. After the heat treatment, the absorbent resin composition (processed absorbent resin) was found to have a water content of 28.5% by weight, a ratio of change of 0% in water content, and a residual monomer content of 21.7 ppm. Subsequently, the processed absorbent resin was removed from the vessel, heat-treated in a fluidized-bed drying device at 80° C. for 3 hours, and sifted with a 20-mesh metallic screen to obtain a thru-20 mesh absorbent resin for comparison. This absorbent resin for comparison was found to have a residual monomer content of 21.8 ppm.

Control 7

One hundred (100) parts of the absorbent resin powder (B) obtained in Referential Example was mixed with 2.0 parts of activated carbon. An aqueous liquid of reducing substance was prepared by dissolving 1 part of monoethanol amine as a reducing substance in 25 parts of water and 2 parts of isopropanol. By the use of a high-speed paddle type mixing device, this aqueous liquid was mixed with the mixture of the absorbent resin powder (B) with the activated carbon. The absorbent resin composition consequently obtained was found to have a water content of 20.0% by weight.

Then, this absorbent resin composition was placed in a cylindrical vessel (1) measuring 10 cm in inside diameter and 10 cm in length, tightly sealed therein, and left standing at normal room temperature for 10 hours. After the standing, the absorbent resin composition (processed absorbent resin) was found to have a water content of 19.6% by weight, a ratio of change of −2% in water content, and a residual monomer content of 28.2 ppm. Subsequently, the processed absorbent resin was removed from the vessel, dried with hot air at 100° C. for 3 hours, and sifted with a 20-mesh metallic screen to obtain a thru-20 mesh absorbent resin for comparison. This absorbent resin for comparison was found to have a residual monomer content of 30.5 ppm.

Control 8

An absorbent resin for comparison was obtained by drying the processed absorbent resin (having a water content of 28.9% by weight) obtained in Example 9 at 150° C. for 3 hours. This absorbent resin for comparison was found to have a residual monomer content of 11.2 ppm.

Control 9

An absorbent resin for comparison was obtained by drying the processed absorbent resin (having a water content of 24.8% by weight) obtained in Example 10 at 180° C. for 2 hours. This absorbent resin for comparison was found to have a residual monomer content of 19.3 ppm.

Control 10

A solution of 328 parts of acrylic acid and 2.6 parts of N,N'-methylene bis-acrylamide in 980 parts of deionized water was adjusted to pH 4.0 with 127.5 parts of sodium bicarbonate. The resultant solution was deprived of dissolved oxygen by introducing a blown stream of nitrogen gas. The aqueous monomer solution and a solution of 0.36 part of azo-bis-amidinopropane dihydrochloride, 0.73 part of potassium persulfate, 1.34 parts of sodium hydrogen sulfite, and 0.06 part of iron (II) gluconate in 120 parts of water were together subjected to stationary polymerization to obtain a gel hydrated polymer. This gel polymer was pulverized. Then, 100 parts of the polymer as solids and 2 parts of hydroxyl amine hydrochloride were mixed. The gel polymer having a water content of 77.0% by weight was dried with hot air at 110° C. for 2 hours, pulverized with a crushing device, and sifted with a 20-mesh metallic screen to obtain a thru-20 mesh absorbent for comparison. The absorbent for comparison was found to have a water content of 4.2% by weight, a ratio of change of −95% in water content, and a residual monomer content of 32.1 ppm.

EXAMPLE 15

One hundred (100) parts of the absorbent resin (B) obtained in Referential Example was mixed with 1.0 part of silicon dioxide (produced by Japan Aerosil K. K. and marketed under trademark designation of "Aerosil 200"). An aqueous liquid of reducing substance was prepared by dissolving 1 part of sodium hydrogen sulfite as a reducing substance in 70 parts of water and 8 parts of isopropanol. By the use of a high-speed paddle type mixing device, this aqueous liquid was mixed with the mixture of the absorbent resin (B) with silicon dioxide. The absorbent resin composition consequently obtained was found to have a water content of 41.3% by weight.

Then, the absorbent resin composition was placed in a cylindrical vessel (1) measuring 10 cm in inside diameter and 10 cm in length, tightly sealed therein, and heat-treated in a furnace at 150° C. for one hour. After the heat treatment, the absorbent resin composition was found to have a water content of 40.2% by weight and a residual monomer content of 0.62 ppm. Subsequently, the absorbent resin composition was removed from the vessel, dried with hot air at 60° C. for 4 hours, and sifted with a 20-mesh metallic screen to obtain a thru-20 mesh absorbent. The absorbent was found to have a residual monomer content of 0.63 ppm.

EXAMPLE 16

One hundred (100) parts of the absorbent resin (B) obtained in Referential Example was mixed with 0.7 part of sodium dialkyl sulfosuccinate as a surfactant (produced by Kao Soap Co., Ltd. and marketed under trademark designation of "Pelex OT-P"). By the use of a high-speed paddle type mixing device, a solution of 1 part of sodium hydrogen sulfite as a reducing substance in 25 parts of water was mixed with the mixture of the absorbent resin (B) with the surfactant. The absorbent resin composition consequently obtained was found to have a water content of 20.5% by weight.

Then, the absorbent resin composition was placed in a cylindrical vessel (1) measuring 10 cm in inside diameter and 10 cm in length, tightly sealed therein, and heat-treated in a furnace at 120° C. for 1 hour. After the heat treatment, the absorbent resin composition was found to have a water content of 20.2% by weight and a residual monomer content of 3.81 ppm. Subsequently, the absorbent resin composition was removed from the vessel, heat-treated with a fluidized-bed drying device at 90° C. for 2 hours, and sifted with a 20-mesh metallic screen to obtain a thru-20 mesh absorbent. This absorbent was found to have a residual monomer content of 4.21 ppm.

EXAMPLE 17

One hundred (100) parts of the absorbent resin (B) obtained in Referential Example was mixed with 1.0 part of silicon dioxide treated to be endowed with hydrophobicity (produced by Japan Aerosil K. K. and marketed under trademark designation of "Aerosil R972"). An aqueous liquid of reducing substance was prepared by dissolving 2 parts of sodium thiosulfate as a reducing substance in 50 parts of water. By the use of a high-speed paddle type mixing device, this aqueous liquid was mixed with the mixture of the absorbent resin (B) with the hydrophobic silicon dioxide. The absorbent resin composition consequently obtained was found to have a water content of 33.5% by weight.

Then, the absorbent resin composition was placed in a well closed paddle drier having a jacket heated to 160° C. and, after 10 minutes a part of the absorbent resin composition was removed. Water content of the absorbent resin composition was 27.2% by weight and residual monomer content was 0.80 ppm. And then it was heated without closure therein for 2 hours to dry. After that, the absorbent was found to have a water content of 7.2% by weight and a residual monomer content of 1.82 ppm.

EXAMPLE 18

One hundred (100) parts of the absorbent resin (B) obtained in Referential Example was mixed with 2.0 parts of aluminum oxide (produced by Degussa K. K. and marketed under trademark designation of "Aluminum Oxide C"). An aqueous liquid of reducing substance was prepared by dissolving 1 part of sodium sulfite as a reducing substance in 120 parts of water and 2 parts of ethanol. By the use of a high-speed paddle type mixing device, this aqueous liquid was mixed with the mixture of the absorbent resin (B) with aluminum oxide. The absorbent resin composition consequently obtained was found to have a water content of 51.2% by weight.

Then, this absorbent resin composition was placed in a cylindrical vessel (1) measuring 10 cm in inside diameter and 10 cm in length and heat-treated in a furnace at 100° C. for 10 hours. After the heat treatment, the absorbent resin composition was found to have a water content of 50.3% by weight and a residual monomer content of 1.25 ppm. Subsequently, the absorbent resin composition was removed from the furnace, heat-treated in a fluidized-bed drying device at 80° C. for 3 hours, and sifted with a 20-mesh metallic screen to obtain a thru-20 mesh absorbent. This absorbent was found to have a residual monomer content of 2.05 ppm.

EXAMPLE 19

One hundred (100) parts of the absorbent resin obtained in Referential Example was mixed with 2.0 parts of activated carbon. An aqueous liquid of reducing substance was prepared by dissolving 1 part of sodium sulfite as a reducing agent in 60 parts of water and 2 parts of isopropanol. By the use of a high-speed padding type mixing device, this aqueous liquid was mixed with the mixture of the absorbent resin composition (B) with the activated carbon. The absorbent resin composition consequently obtained was found to have a water content of 38.1% by weight.

Then, this absorbent resin composition was placed in a furnace of the type adapted to admit a blown stream of steam and heat-treated therein with a stream at 180° C. for 2 hours. After the heat treatment, the absorbent resin composition was found to have a water content of 37.1% by weight and a residual monomer content of 0.05 ppm Subsequently, the absorbent resin composition was removed from the vessel, dried with hot air at 50° C. for 10 hours, and sifted with a 20-mesh metallic screen to obtain a thru-20 mesh absorbent. This absorbent was found to have a residual monomer content of 0.08 ppm.

EXAMPLE 20

One hundred (100) parts of the absorbent resin (B) obtained in Referential Example was mixed with 2.0 parts of fine powder of polymethyl methacrylate. By the use of a high-speed paddle type mixing device, a solution of 1 part of sodium hydrogen sulfite as a reducing substance in 120 parts of water was mixed with the mixture of the absorbent resin (B) with polymethyl methacrylate. The absorbent resin composition consequently obtained was found to have a water content of 55.2% by weight.

Then, the absorbent resin composition was placed in a cylindrical vessel (1) measuring 10 cm in inside diameter and 10 cm in length, tightly sealed therein, and heat-treated in a furnace at 200° C. for one hour. After the heat treatment, the absorbent resin composition was found to have a water content of 53.8% by weight and a residual monomer content of 0.21 ppm. Subsequently, the absorbent resin composition was removed from the vessel, heat-treated in a fluidized-bed drying device at 90° C. for 2 hours, and sifted with a 20-mesh metallic screen to obtain a thru-20 mesh absorbent. This absorbent was found to have a residual monomer content of 0.73 ppm.

The working examples and controls described above support the following conclusion. For the purpose of decreasing the residual monomer content in an absorbent resin, it is very important that the amount of water existing during the addition of a substance capable of reacting with the residual monomer and the ratio of change in water content during the subsequent step of heat treatment should be retained within respectively specified ranges. No efficient decrease of the residual monomer content is attained when the amount of water to be added is unduly small or unduly large. Even if the amount of water to be added is optimum, the residual monomer content is not efficiently decreased when the absorbent resin is immediately dried.

The efficiency with which the residual monomer content in an absorbent resin can be conspicuously exalted by optimizing the amount of water existing during the addition of a substance capable of reacting with the residual monomer and performing the subsequent step of heat treatment while retaining the ratio of change in water content within a specific range. This invention produces an absorbent of highly safe quality containing virtually no residual monomer. Thus, it ensures stable and highly efficient production of an absorbent enjoying highly safe quality.

For the purpose of decreasing the residual monomer content in an absorbent resin powder, the requirement that the amount of water existing during the addition of a substance capable of reacting with the residual monomer and the change in the water content during the subsequent step of heat treatment should remain within respectively specific ranges is very important and the temperature and duration of the heat treatment are also important. No efficient decrease of the residual monomer content is obtained when the amount of water added is unduly small or unduly large Even if the amount of water added is optimum, the residual monomer content is not efficiently decreased when the absorbent resin is immediately dried or it is dried at an unduly high temperature.

From the results given above, it is concluded that the residual monomer content can be decreased with high efficiency by optimizing the amount of water added during the addition of a substance capable of reacting the residual monomer, carrying out the heat treatment while retaining the water content within a specific range, and subsequently performing the operation of drying at the lowest possible temperature. It has been ascertained that this invention produces an absorbent resin containing virtually no residual monomer. Thus, this invention allows an absorbent resin of highly safe quality to be produced stably and efficiently.

The absorbent of this invention has contained in an absorbent resin substantially no detectable residual monomer. None of the conventional techniques has succeeded in producing an absorbent of this high quality. By making the most of these characteristic properties, therefore, the absorbent or absorbent resin which is obtained by this invention can be ideally utilized in applications such as absorbent materials for disposable diapers, sanitary napkins, or other sanitary materials, water-retaining materials for medical treatments, water-retaining materials for agronomic operations, and desorbing materials for various industries which invariably necessitate the ability to absorb water or the ability to retain water.

What is claimed is:

1. A method for treating an absorbent resin comprising:
   (a) a step of adding to an absorbent resin a substance which reacts with the residual monomer in said absorbent resin thereby forming an absorbent resin composition having a water content in the range of 10 to 70% by weight; and
   (b) a step of heat-treating said absorbent resin composition in a tightly closed state and/or under a high humid atmosphere at a temperature in the range of 100° C. to 200° C. for no less than 10 minutes while keeping the change in the ratio of the water content of the absorbent resin within 20%;
   wherein said method provides an absorbent resin having a residual monomer content of less than or equal to 2 ppm.

2. A method according to claim 1, wherein said absorbent resin powder is a partially neutralized cross-linked polyacrylic acid.

3. A method according to claim 1, wherein said substance which reacts with the residual monomer in said absorbent resin powder is at least one member selected from the group consisting of nitrogen-containing compounds, sulfurous acid (and salts thereof), hydrogen sulfite (and salts thereof), phosphorous acid (and salts thereof), pyrosulfurous acid (and salts thereof), hypophosphorous acid (and salts thereof), and thiosulfuric acid (and salts thereof).

4. A method according to claim 1, wherein said substance which reacts with the residual monomer in said absorbent resin powder is at least one reducing substance selected from the group consisting of sulfurous acid (and salts thereof), hydrogen sulfite (and salts thereof), pyrosulfurous acid (and salts thereof), and thiosulfuric acid (and salts thereof).

5. A method according to claim 1, wherein said absorbent resin treated at the step of (a) has a water content in the range of 20 to 60% by weight.

6. A method according to claim 1, wherein the ratio of change in water content at the step of (b) is within 10%.

7. A method according to claim 1, wherein the temperature of the heat treatment at the step of (b) is in the range of 120° to 180° C.

8. A method according to claim 1, wherein the period of the heat treatment at the step of (b) is in the range of 10 minutes to 10 hours.

9. A method according to claim 1, wherein said absorbent resin composition in step (a) further contains water-insoluble particulate substances, surfactants, or organic solvents.

10. A method for the production of an absorbent resin comprising (a) a step of adding to an absorbent resin powder a substance which reacts with a residual monomer in said absorbent resin powder thereby forming an absorbent resin composition having a water content in the range of 25 to 55% by weight, (b) a step of heat-treating said absorbent resin composition at a temperature in the range of 120° to 200° C. for a period of not less than 10 minutes while retaining the water content of said absorbent resin composition in said range thereby obtaining a processed absorbent resin, and (c) a step of drying said processed absorbent resin at a temperature not exceeding 120° C., wherein said method provides an absorbent resin having a residual monomer content of less than or equal to 2 ppm.

11. A method according to claim 10, wherein said absorbent resin powder is a partially neutralized cross-linked polyacrylic acid.

12. A method according to claim 10, wherein said substance which reacts with the residual monomer in said absorbent resin powder is at least one member selected from the group consisting of nitrogen-containing compounds, sulfurous acid (and salts thereof), hydrogen sulfite (and salts thereof), phosphorous acid (and salts thereof), pyrosulfurous acid (and salts thereof), hypophosphorous acid (and salts thereof), and thiosulfuric acid (and salts thereof).

13. A method according to claim 10, wherein said substance which reacts with the residual monomer in said absorbent resin powder is at least one reducing substance selected from the group consisting of sulfurous acid (and salts thereof), hydrogen sulfite (and salts thereof), pyrosulfurous acid (and salts thereof), and thiosulfuric acid (and salts thereof).

14. A method according to claim 10, wherein the temperature of the heat treatment at the step of (b) is in the range of 150° to 170° C.

15. A method according to claim 10, wherein the period of the heat treatment at the step of (b) is in the range of 10 minutes to 10 hours.

16. A method according to claim 10, wherein the temperature of the drying treatment at the step of (c) is in the range of 50° to 100° C.

17. A method according to claim 10, wherein the drying temperature at the step of (c) is in the range of 60° to 80° C.

18. A method according to claim 10, wherein said absorbent resin composition in step (a) further contains water-insoluble particulate substances, surfactants, or organic solvents.

19. A method according to claim 10, wherein the drying at the step of (c) is carried out until the water content reaches at least 15% by weight.

20. A method for the production of an absorbent resin comprising (a) a step of adding to an absorbent resin powder a substance which reacts with a residual monomer in said absorbent resin powder thereby forming an absorbent resin composition having a water content in the range of 25 to 55% by weight, (b) a step of heat-treating said absorbent resin composition at a temperature in the range of 120° to 200° C. for a period of not less than 10 minutes while retaining the water content of said absorbent resin composition in said range thereby obtaining a processed absorbent resin, and (c) a step of drying said processed absorbent resin at a temperature not exceeding 120° C. wherein said process provides an absorbent resin having a residual monomer content of less than or equal to 2 ppm.

21. A method for treating an absorbent resin comprising:

(a) a step of adding to an absorbent resin a substance which reacts with the residual monomer in said absorbent resin thereby forming an absorbent resin composition having a water content in the range of 10 to 70% by weight;

(b) a step of heat-treating said absorbent resin composition in a tightly closed state and/or under a high humid atmosphere at a temperature in the range of 120° C. to 200° C. for no less than 10 minutes while keeping the change in the ratio of the water content of the absorbent resin within 20%; and (c) a step of drying said processed absorbent resin at a temperature not exceeding 120° C., wherein said method provides an absorbent resin having a residual monomer content of less than or equal to 2 ppm.

* * * * *

UNITED STATES PATENT AND TRADEMARK OFFICE
CERTIFICATE OF CORRECTION

PATENT NO. : 5,866,678
DATED : February 2, 1999
INVENTOR(S) : KAJIKAWA, et al.

It is certified that error appears in the above-identified patent and that said Letters Patent is hereby corrected as shown below:

At Column 11, line 44, delete "B972" and insert --R972--.

At Column 12, line 25, delete "sulfosuocinate" and insert --sulfosuccinate--.

Signed and Sealed this

Twenty-third Day of November, 1999

*Attest:*

Q. TODD DICKINSON

*Attesting Officer*  *Acting Commissioner of Patents and Trademarks*